(12) United States Patent
Fournier et al.

(10) Patent No.: US 11,298,198 B2
(45) Date of Patent: Apr. 12, 2022

(54) ROBOTIC MODULE FOR DRIVING AN ELONGATE FLEXIBLE MEDICAL MEMBER

(71) Applicant: ROBOCATH, Rouen (FR)

(72) Inventors: Bruno Fournier, Saint Ouen (FR); Julien Maurel, Bonsecours (FR); Sébastien Deboeuf, Bonsecours (FR); Phillippe Bencteux, Saint Martin du Vivier (FR)

(73) Assignee: ROBOCATH, Rouen (FR)

( * ) Notice: Subject to any disclaimer, the term of this patent is extended or adjusted under 35 U.S.C. 154(b) by 790 days.

(21) Appl. No.: 16/060,240

(22) PCT Filed: Dec. 6, 2016

(86) PCT No.: PCT/FR2016/053231
§ 371 (c)(1),
(2) Date: Jun. 7, 2018

(87) PCT Pub. No.: WO2017/098138
PCT Pub. Date: Jun. 15, 2017

(65) Prior Publication Data
US 2018/0353250 A1 Dec. 13, 2018

(30) Foreign Application Priority Data
Dec. 7, 2015 (FR) .................................... 15 61937

(51) Int. Cl.
*A61B 34/35* (2016.01)
*A61B 34/00* (2016.01)
(Continued)

(52) U.S. Cl.
CPC .............. *A61B 34/35* (2016.02); *A61B 34/30* (2016.02); *A61B 34/76* (2016.02);
(Continued)

(58) Field of Classification Search
CPC ........................ A61B 34/30; A61B 2034/301
See application file for complete search history.

(56) References Cited

U.S. PATENT DOCUMENTS

| 2007/0197939 | A1† | 8/2007 | Wallace |
| 2013/0035537 | A1 | 2/2013 | Wallace et al. |
| (Continued) | | | |

FOREIGN PATENT DOCUMENTS

| EP | 2 216 068 | 8/2010 |
| EP | 2 875 792 | 5/2015 |
| WO | WO 99/45994 | 9/1999 |

OTHER PUBLICATIONS

International Search Report, PCT/FR2016/053231, dated Feb. 7, 2017.
(Continued)

*Primary Examiner* — Todd J Scherbel
(74) *Attorney, Agent, or Firm* — Nixon & Vanderhye

(57) ABSTRACT

A robotic module for driving an elongate flexible medical member includes: movable drive members alternately positioned in a drive configuration in which the drive members are sufficiently close together to be able to drive the elongate flexible medical member, and in a free configuration in which the drive members are sufficiently far apart so as to no longer be able to drive the elongate flexible medical member, a control member controlling movement of the movable drive members into the drive configuration in which the elongate flexible medical member is driven, and a reverse movement into the free configuration, a stress sensor measuring stress on at least one of the drive members, and a user interface linked to the stress sensor so as to receive the measured stress from the stress sensor and suitable for providing a signal representative of the measured stress to the user of the robotic module.

23 Claims, 9 Drawing Sheets

(51) Int. Cl.
*A61M 25/01* (2006.01)
*A61B 34/30* (2016.01)
*A61B 90/00* (2016.01)
*A61B 17/00* (2006.01)

(52) U.S. Cl.
CPC ............... *A61M 25/0113* (2013.01); *A61B 2017/00119* (2013.01); *A61B 2034/301* (2016.02); *A61B 2034/303* (2016.02); *A61B 2090/065* (2016.02); *A61B 2090/376* (2016.02); *A61M 2205/332* (2013.01)

(56) References Cited

U.S. PATENT DOCUMENTS

2014/0276939 A1† 9/2014 Kokish
2015/0297864 A1† 10/2015 Kokish

OTHER PUBLICATIONS

D. Wang et al., A novel design of a wearable device for measuring force and torque in vascular surgery, 2013 IEEE Int. Conf. on Robotics and Automation (ICRA), published 2013, pp. 2374-2379.†

† cited by third party

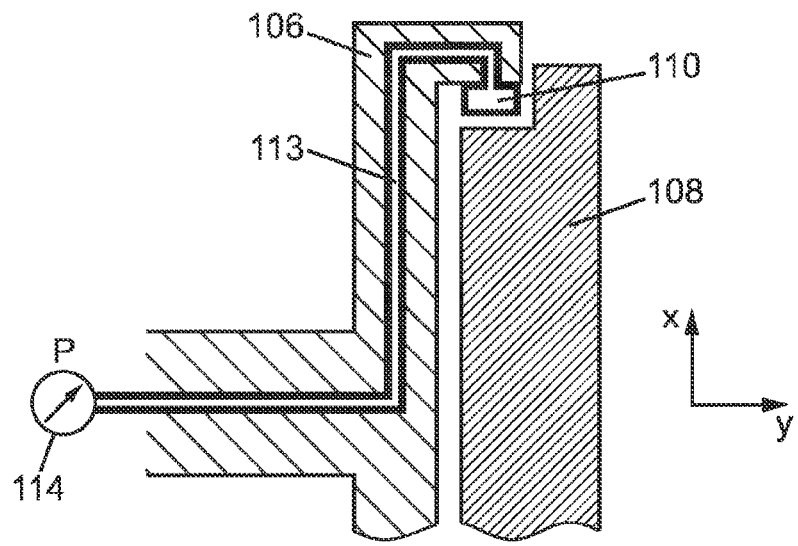
FIG. 14
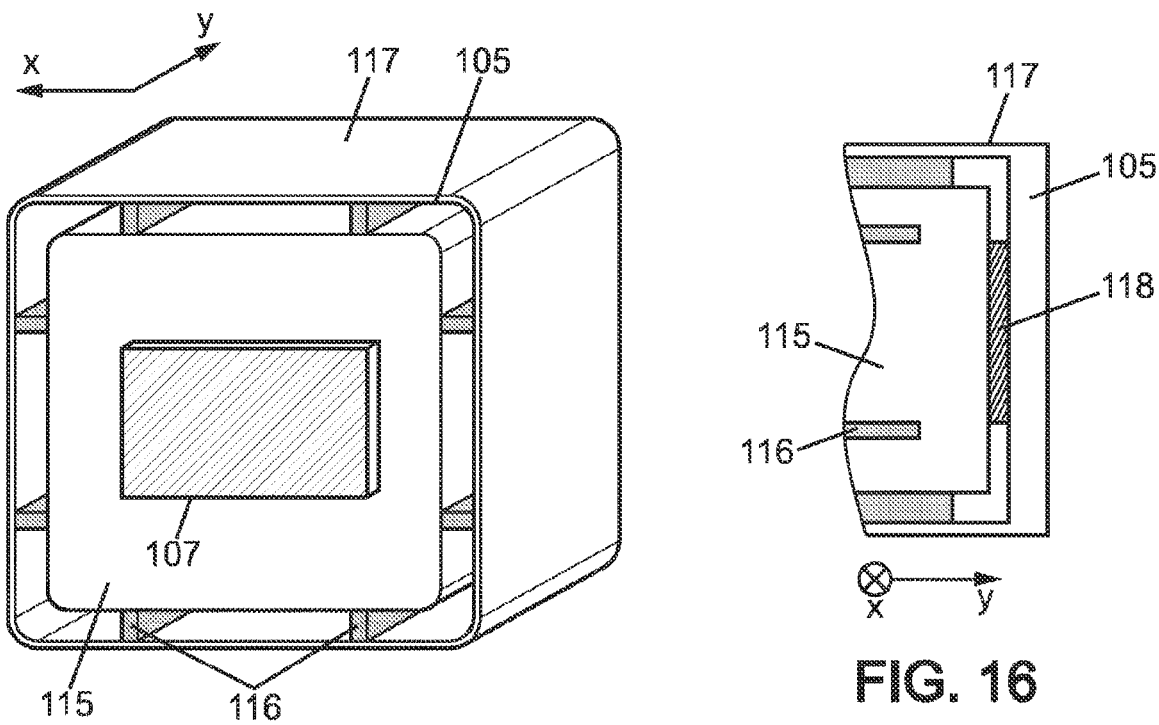
FIG. 15
FIG. 16

ROBOTIC MODULE FOR DRIVING AN ELONGATE FLEXIBLE MEDICAL MEMBER

The present invention relates to robotic modules for driving elongate flexible medical members, for example a catheter and/or a guide for this catheter. In the following, the example of a guide for this catheter or an elongate flexible medical member will be used interchangeably, but are equally applicable to either a catheter guide or to another type of elongate flexible medical member.

BACKGROUND OF THE INVENTION

Manual insertion of a catheter or guide into a patient is a relatively conventional surgical procedure. However, as this procedure is monitored by X-rays, the surgeon in charge of the procedure is exposed to significant radiation if he or she performs such an operation on many patients.

In order to reduce the risks for the surgeon, it is desirable to robotize such insertion. Such robotization is complex because it is difficult to grip the catheter. The catheter is bathed in preservation liquid and must remain sterile. It is also desirable to be able to control alternating and/or simultaneous translational and rotational movements of the catheter. The reliability of these robotic systems is a determining factor.

However, during advancement of the elongate flexible medical member within the body of the patient, this elongate flexible medical member will either advance freely and meet normal resistance not requiring special intervention by the user of the module for driving the elongate flexible medical member, or may be hindered or blocked in its advancement after encountering an obstacle presenting abnormally high resistance that requires, for optimal advancement of the elongate flexible medical member, intervention or at least an appropriate reaction by the user of this module for driving the elongate flexible medical member.

Today, there is really nothing provided to assist the user of the module for driving the elongate flexible medical member, who has to manage alone, relying solely on his or her experience to sense, perceive, and verify the different areas of advancement likely to offer abnormally high resistance to the advancement of the elongate flexible medical member, and in particular to leave the remote control station at certain points and check next to the patient that the advancement is occurring without problems, standing ready to manipulate the elongate flexible medical member directly with his or her fingers in the patient, without the aid of the module for driving the elongate flexible medical member, in order to allow the elongate flexible medical member to pass smoothly beyond an obstacle.

In the case of normal advancement of the elongate flexible medical member in the artery or vein in which it is being moved, the elongate flexible medical member exerts only normal and usual stress on the drive members of the elongate flexible medical member, this normal stress value either being known or conventionally determinable.

In the case of abnormal progression of the elongate flexible medical member within the artery or vein in which it is being moved, the elongate flexible medical member exerts abnormal and unusual stress, particularly abnormally high, on the drive members of the elongate flexible medical member, this abnormal stress value neither being known nor conventionally determinable since by definition the encountered obstacle is unusual. In this case, passage through the obstacle encountered by the elongate flexible medical member is more difficult for the user of the module for driving the elongate flexible medical member, and may require the user to leave the remote control station to go touch the elongate flexible medical member, manually determine the nature of the obstacle to be traversed by the elongate flexible medical member, and manually move the elongate flexible medical member through the obstacle. At worst, the user is unaware of anything and the elongate flexible medical member can damage the artery or vein by forcing through the obstacle which has not been identified or whose nature has not been correctly evaluated.

SUMMARY OF THE INVENTION

The object of the present invention is to provide a module for driving the elongate flexible medical member, which at least partially overcomes the above disadvantages.

More particularly, the invention aims to provide a module for driving an elongate flexible medical member that automates the passage of the elongate flexible medical member through an obstacle by providing the user with feedback representative of the abnormal level of stress exerted by the elongate flexible medical member on the drive members of the elongate flexible medical member by the ricochet due to interference or blockage encountered by this elongate flexible medical member during passage through an obstacle.

For this purpose, the invention proposes providing a signal representative of the stress exerted by the elongate flexible medical member on all or part of the drive members of the elongate flexible medical member. The more this signal representative of the stress exerted by the elongate flexible medical member on all or part of the drive members of the elongate flexible medical member is accurate and properly reproduced for the user, the better the user can easily and remotely manage, in other words while more often or even always remaining in the remote control station, the passage through the obstacle by the elongate flexible medical member during its advancement, and in any case drastically reducing or even entirely eliminating the risk of artery or vein damage by the elongate flexible medical member during its advancement.

To this end, the present invention provides a robotic module for driving an elongate flexible medical member, comprising: a pair of movable drive members that can be alternately positioned in a drive configuration in which the drive members are sufficiently close together to be able to drive the elongate flexible medical member, and in a free configuration in which the drive members are sufficiently far apart so as to no longer be able to drive the elongate flexible medical member, a control member suitable for controlling, in a repeated cyclic manner, a movement of the pair of movable drive members into the drive configuration in which the elongate flexible medical member is driven, and a reverse movement of the pair of movable drive members into the free configuration in which the elongate flexible medical member is not driven, a stress sensor constructed and arranged to measure the stress exerted by the elongate flexible medical member on at least one of the drive members, and a user interface linked to the stress sensor so as to receive the measured stress from the stress sensor and suitable for providing a signal representative of this measured stress to the user of the robotic module.

According to preferred embodiments, the invention comprises one or more of the following features which may be used individually or any combination.

Preferably, said signal comprises an indication that a threshold is exceeded by the measured stress.

Thus, when the obstacle becomes a significant interference, the user is notified and can immediately act in an appropriate manner, which represents a drive module assisting the user at least for the most difficult cases, meaning serious obstacles to be passed through by the elongate flexible medical member.

Preferably, said signal comprises an indication of a value proportional to the value of this measured stress.

Thus, when the obstacle becomes an interference, the user is warned very early and very accurately, which allows the user not only to act immediately in an appropriate manner, but possibly also to anticipate a blockage or significant interference before or immediately before it occurs, which represents a drive module assisting the user at least for all cases and in near real-time, thus enabling an optimal and often preemptive response.

Preferably, said signal takes the form of at least one visual and/or audible alarm.

This provides assistance to the user which enables the user to become aware of a particular difficulty during advancement of the elongate flexible medical member and to react appropriately. The visual alarm may be binary, such as a red flashing light, or progressive such as a bar graph that is filled as the stress exerted by the elongate flexible medical member on the drive members of this elongate flexible medical member increases. The audible alarm may be binary, such as a triggered siren, or progressive, such as an increasingly loud and/or high pitched sound as the stress exerted by the elongate flexible medical member on the drive members of this elongate flexible medical member increases.

Preferably, said signal is in the form of at least one haptic feedback to the user of the robotic module, representative of this measured stress, preferably corresponding to this measured stress, even more preferably proportional to this measured stress. Haptic feedback corresponding to this measured stress is haptic feedback which, for example by resistance of the user interface to manipulation by the user without being proportional to the measured stress, is also not binary, but offers a certain progression in the level of feedback corresponding to the increase in the stress level, without being proportional. This haptic feedback can be an increasing function of the measured stress, possibly with plateaus offering a system of multiple thresholds, or a strictly increasing function varying as the square or as the square root of the measured stress, or of the increase in the measured stress relative to normal stress.

This is therefore the most effective aid, because it gives the user sensations most similar to what he or she would experience if actually manually inserting the elongate flexible medical member in the patient while remaining close by. This haptic feedback, such as resistance in the joystick for example, provides improved ergonomics, as the user's hand will be able to adapt automatically without requiring prior analysis related to detection of a visual or audible alarm. Maximized safety is of course provided when the haptic feedback is combined with a simultaneous visual alarm and/or audible alarm.

Preferably, the haptic feedback corresponding to the measured stress is adapted to reproduce a variation in the measured stress as low as 0.1 Newton.

Thus any resistance, even slight, of the elongate flexible medical member is transmitted immediately and accurately, enabling the user to adapt his or her reaction more quickly and accurately or even to anticipate the difficulty looming on the horizon.

Preferably, the robotic module for driving an elongate flexible medical member further comprises: an abnormal stress level estimator adapted to calculate the difference between said measured stress and a nominal stress corresponding to normal driving of the elongate flexible medical member by the drive members, the exceeding of a threshold by said difference corresponding to an abnormal level of stress, a warning device emitting a visual and/or audible alert if said threshold is exceeded.

Preferably, said abnormal stress level estimator is adapted to calculate the difference between said measured stress and a nominal stress corresponding to normal driving of the elongate flexible medical member by the drive members, and if the value of said difference exceeds a given threshold this corresponds to abnormal resistance of the elongate flexible medical member to the force exerted on it by the drive members, resulting in insufficient movement of the elongate flexible medical member.

The presence of a visual or audible alarm when a threshold is exceeded, which in practice will correspond to the detection of an already significant obstacle, will "force" the user to become aware of it and will therefore urge the user to react quickly. This helps the user to better control the module for driving the elongate flexible medical member. This improved module for driving the elongate flexible medical member is therefore a more efficient and safe device for the user, who will therefore be more efficient in his or her advancement of the elongate flexible medical member within the patient.

Preferably, said stress sensor indirectly measures the stress exerted by the elongate flexible medical member on at least one of the drive members.

In this first indirect type of stress detection, the remote detection makes it possible for the various elements required to perform this stress detection not to be close to the drive system of the elongate flexible medical member, and therefore close to the patient. The interference caused near the patient is therefore minimal or non-existent.

Preferably, said stress sensor measures the current consumed by said drive member. Advantageously, the portion required to compensate for the parasitic force generated by the transmission mechanism will be removed from the consumed current.

As the consumed electric current is a pre-existing parameter to the stress detection, few elements need to be added, and in any case no elements at the drive system of the elongate flexible medical member itself, which simplifies the stress detection chain.

Preferably, the robotic module for driving the elongate flexible medical member also comprises a plurality of actuators arranged to respectively transmit movements in multiple spatial directions, advantageously in three directions perpendicular to each other, directly towards the same drive member. As a result, the fact that some or all of the actuators are prevented from transmitting their movement to the drive member indirectly, meaning via another actuator or via the platform of another actuator, reduces the weight, inertia, friction, and the number of intermediate parts, thus significantly improving the accuracy of this type of indirect detection which is otherwise intrinsically less accurate than direct types of detection.

Preferably, said stress sensor directly measures the stress exerted by the elongate flexible medical member on at least one of the drive members.

In this second direct type of stress detection, "close" detection requires bringing the various elements required to perform this stress detection close to the drive system of the elongate flexible medical member, and therefore close to the patient. But the advantage associated with this close detection lies in improved detection accuracy in comparison to the first indirect type of stress detection.

Preferably, said stress sensor is a strain gauge arranged to directly measure the stress exerted by the elongate flexible medical member on at least one of the drive members.

The accuracy of this type of direct measurement, close to the drive member of the elongate flexible medical member undergoing the stress exerted by this elongate flexible medical member when against the obstacle encountered by this elongate flexible medical member, allows improving accuracy while maintaining a good level of simplicity for the entire stress detection chain.

Preferably, said strain gauge is arranged between said drive member and the frame of the robotic module and is in contact with both said drive member and said frame of the robotic module.

The arrangement of the elements of the strain gauge is simpler and more robust.

Preferably, said strain gauge is arranged between two parts of said drive member and is in simultaneous contact with the two parts of said drive member.

The arrangement of the elements of the strain gauge is more fragile, but accuracy is further improved.

Preferably, said drive member comprises a pad intended to come into contact with the elongate flexible medical member, and a pad holder transmitting the movement to the pad, said strain gauge being arranged between said pad and said pad holder.

This embodiment where the strain gauge is closer to the part of the drive member of the elongate flexible medical member that is in direct contact with the elongate flexible medical member itself, while requiring small elements for insertion into reduced spaces, offers further improvement in the accuracy obtained in the measurement of the stress exerted by the elongate flexible medical member on the drive member of this elongate flexible medical member.

Preferably, said strain gauge is arranged between the periphery of said pad and the periphery of said pad holder.

Preferably, said strain gauge is arranged between the bottom of said pad and the bottom of said pad holder.

Preferably, said stress sensor is a Hall effect sensor arranged to measure the movement of a magnet arranged on one of the drive members.

The use of a magnet requires precise arrangement of the detection elements and their relative position, but offers the advantage of enabling stress detection without contact.

Preferably, the robotic drive module comprises a base, said drive members each have a driving surface, in said drive configuration the driving surfaces of the drive members of the pair of drive members are engaged with the elongate flexible medical member to be driven and are arranged one on either side thereof, in a free configuration the driving surface of the drive members of the pair of drive members is not engaged with the elongate flexible medical member, the pair of drive members being movably mounted relative to the base with a degree of freedom between a first and a second position, said control member is suitable for controlling, in a repeated cyclic manner, a movement relative to the base of the drive members of the pair of drive members, from the first to the second position into a drive configuration, thereby driving the elongate flexible medical member relative to the base, and a reverse movement relative to the base of the drive members of the pair of drive members, from the second to the first position into a free configuration in which the elongate flexible medical member is not driven relative to the base.

Preferably, the base is a first base, the pair of drive members is a first pair of drive members, the robotic module further comprising: a second pair of drive members each having a driving surface, the second pair of drive members able to be alternately positioned in a drive configuration in which the driving surfaces of the drive members of the second pair of drive members engage with the elongate flexible medical member to be driven and are arranged one on either side thereof, and in a free configuration in which the driving surface of the drive members of the second pair of drive members does not engage with the elongate flexible medical member, the second pair of drive members being movably mounted relative to the base with a degree of freedom between a first and a second position, said control member being further suitable for controlling, in a cyclic repeated manner, a movement relative to the base of the drive members of the second pair of drive members, from the first to the second position into a drive configuration, thereby driving the elongate flexible medical member relative to the base, and a movement relative to the base of the drive members of the second pair of drive members, from the second to the first position into a free configuration in which the flexible medical member is not driven relative to the base, said control member being suitable for controlling the movements of the drive members of the first and second pairs in a synchronized manner.

Preferably, the translation of the drive members in a direction transverse to the local longitudinal direction of the elongate flexible medical member and in opposite directions of movement is adapted to allow the elongate flexible medical member to roll on the driving surfaces about the local longitudinal direction of the elongate flexible medical member.

Preferably, the measured stress corresponds to the stress exerted by the elongate flexible medical member on at least one of the drive members along only the axis of movement of the elongate flexible medical member.

Thus, the stress detection device can be relatively simple in its structure and arrangement, and the essential information is still obtained because the resistance encountered by a filiform elongate flexible medical member in its direction of advancement will essentially result in stress exerted along the axis of movement of the elongate flexible medical member.

Preferably, the robotic module for driving an elongate flexible medical member according to the invention comprises one or more actuators arranged to respectively transmit movements in several spatial directions towards the same drive member according to one or more reversible transmission mechanisms.

Thus, if the actuator makes a first movement to transmit a force to the drive member which then performs a second movement, and conversely if it is this drive member that performs this second movement due to momentum from other than the actuator, this will then automatically cause the actuator to perform this first movement.

During normal operation it is the actuator that drives the drive member (which in turn drives the catheter), but this driving is reversible, a movement (caused by something other than the actuator) of the drive member driving the actuator.

The reversible nature of a transmission mechanism can also be defined in the absence of motion. Thus, if the actuator exerts a force on the transmission mechanism, this is transmitted to the drive member. A consequence of the reversibility of the transmission mechanism is then that a force exerted on the drive member by an external element other than the actuator, and retransmitted to the transmission mechanism, has the consequence of exerting the same force on the actuator. The reversible nature of the transmission of motion between the actuator and the drive member results in better accuracy and is better representative of the signal which is representative of the stress measured by the stress sensor and which is provided to the user of the robotic module by the user interface, in particular when this signal is in the form of haptic feedback.

In practice, a motion transmission system can never be perfectly reversible, for example because of friction, operating clearance, and inertia.

BRIEF DESCRIPTION OF THE DRAWINGS

Other features and advantages of the invention will be apparent from the following description of one of its embodiments, given by way of non-limiting example, with reference to the accompanying drawings.

In the drawings.

DETAILED DESCRIPTION OF THE PREFERRED EMBODIMENTS

Figure 1:
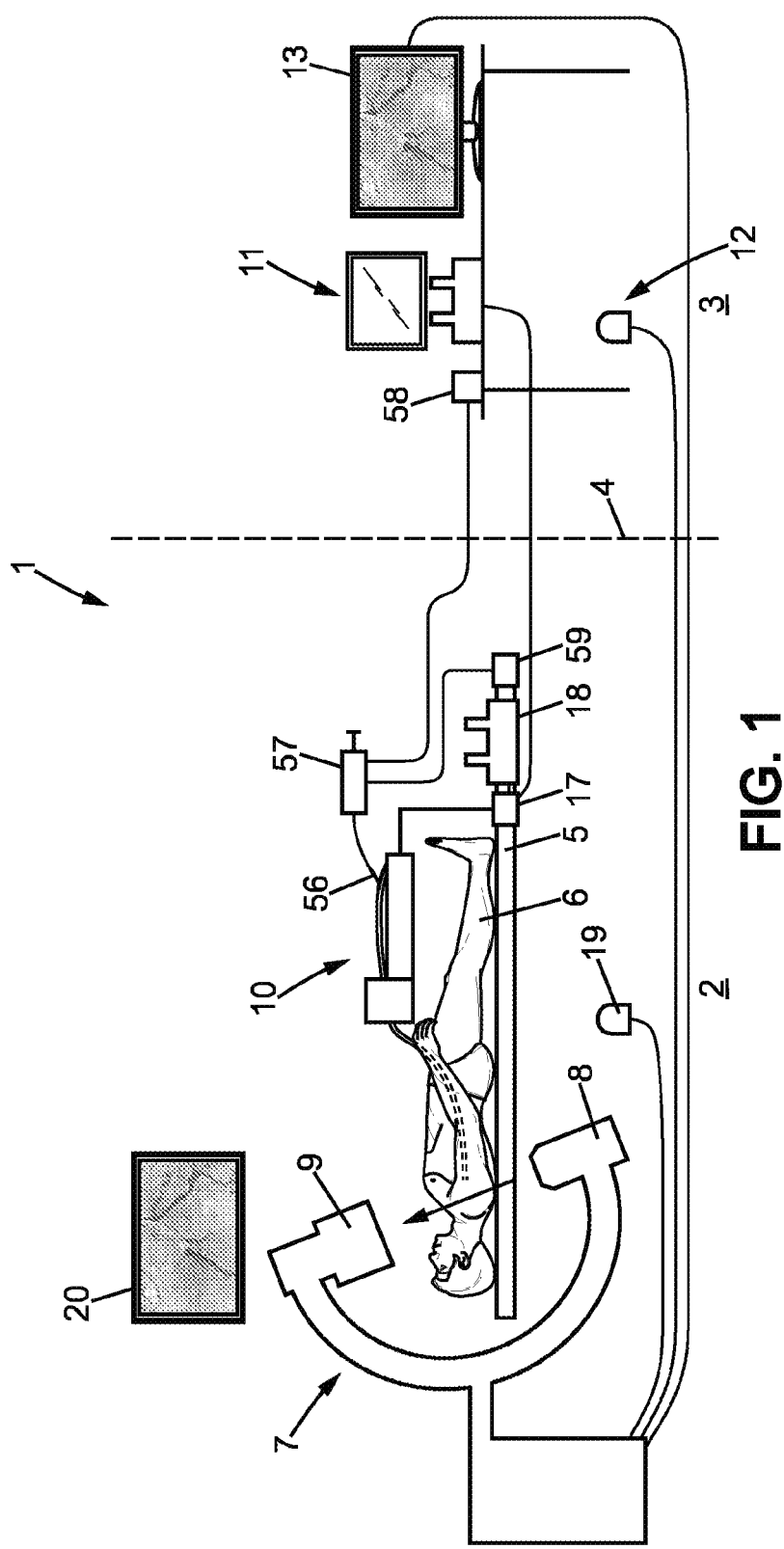
FIG. 1 is a schematic side view of a robotic arteriography system.

FIG. 1 schematically represents an arteriography facility 1. The arteriography facility 1 is divided into two separate locations, an operating room 2 and a control room 3. The control room 3 may be close to the operating room 2 and separated from it by a simple wall 4 that is radiopaque, or remote. The equipment of the operating room 2 and control room 3 are functionally interconnected via a wired or wireless connection or network, etc.

The operating room 2 comprises an operating table 5 receiving a patient 6. The operating room 2 may also comprise a medical imager 7, in particular an X-ray imager, comprising a source 8 and a detector 9 arranged one on each side of the patient, possibly movable relative to the patient.

The arteriography facility 1 comprises a robot 10 located in the operating room 2.

The arteriography facility 1 comprises a control station 11 located in the control room 3. The control station 11 controls the robot 10 remotely. The arteriography facility 1 may also comprise, in the control room 3, one or more remote controls 12 for the imager 7, communicating with the imager 7 in order to control it remotely. The arteriography facility 1 may also comprise a screen 13 located in the control room 3, communicating with the imager 7, for displaying in the control room 3 in real time the images acquired by the imager 7.

The robot 10 may comprise a container 14 adapted to contain an elongate flexible medical member 15 to be introduced into the body of a patient. The elongate flexible medical member 15 may be, for example, a member to be inserted into a canal of a patient and to be moved in this canal, particularly an artery or a vein of a patient, through a desilet which provides an opening for access to the patient. The elongate flexible medical member may be a catheter. Alternatively, the elongate flexible medical member may be a catheter guide. A guide is generally of smaller transverse diameter than the catheter, which has a generally hollow portion near the patient or along its entire length so that the guide can move inside it, in particular inside the patient's body. The guide may also comprise a curved end, as will be described in more detail below.

The robot 10 may comprise a drive module 16 for the elongate flexible medical member 15. The drive module 16 can be controlled from the control station 11 to drive the elongate flexible medical member relative to the patient along at least one degree of freedom, as will be described in detail below. The drive module may comprise a communication unit 17 used for interfacing with the control station 11. If necessary, the robot 10 may comprise a local control unit 18, for controlling the robot from the operating room 2 if necessary.

One will note that all the commands and feedback available in the control room 3 may also be available in the operating room 2 in order to carry out an operation locally, for example such as controls 19 for the imager and a screen 20 for displaying the images captured by the imager 7.

The hollow elongate flexible medical member may be connected to a connector 56 for injecting a contrast enhancing imaging product into the elongate flexible medical member. The arteriography facility may comprise a contrast medium injector 57 connected to the connector 56, controllable by controls 58 arranged in the control room 3. Controls 59 for the contrast agent injector may also be locally present in the operating room 2.

In the following, the reference 15 will alternately be used to designate the guide 15", the catheter 15', or generally an elongate flexible medical member to be inserted into the body of a patient. For example, it may be a surgical catheter. Such a surgical catheter may be of smaller diameter than the catheter, so as to be guided inside the latter, coaxially inside the patient, and may be hollow so as to be guided on the guide inside the patient.

Figure 2A:
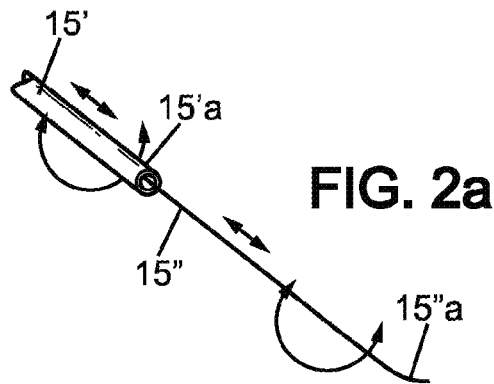
FIGS. 2a-2c are diagrams illustrating the movement modes of the members to be driven.

FIG. 2*a* shows the various degrees of freedom possible with the present system. The guide 15" is shown with its front end 15" slightly curved with respect to the main longitudinal axis of the guide, with an opening at the front end 15'*a* of the catheter 15'. The catheter 15' can be subjected to two distinct movements:

translation along its longitudinal axis,
rotation about its longitudinal axis.

These movements can be generated in either direction.

Where appropriate, the catheter 15' may be subjected to a combined movement of the two basic movements described above.

If desired, the catheter 15' may be subjected to two combined movements of the two basic movements described above, in different combinations.

What has been described above concerning the catheter also applies to the guide.

In some cases, the catheter itself is provided with a curved end, either to enable navigation according to the same principle as a guide, or to facilitate positioning in an anatomical area having a particular curvature.

Figure 2B:
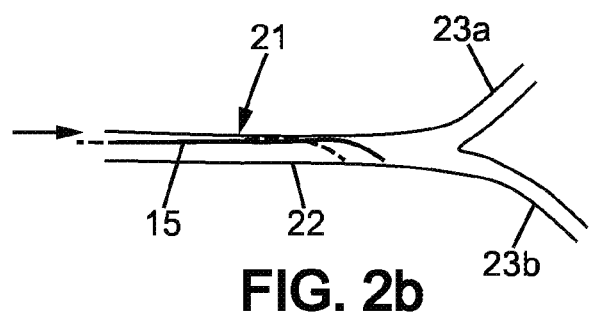
Figure 2C:
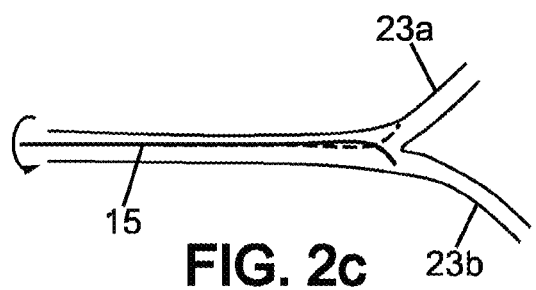

In FIG. 2*b*, an artery 21 of a patient is represented, comprising a main trunk 22 and two branches 23*a*, 23*b* opening into the main trunk. FIG. 2*b* illustrates the translational movement of an elongate flexible medical member 15 (here a guide 15") between a retracted position represented by dotted lines and an advanced position represented by solid lines. In FIG. 2*c*, in the same artery, a rotation of the elongate flexible medical member 15 is represented, between a first position represented by dotted lines, where the elongate flexible medical member is ready for translational movement in the direction of branch 23*a*, and a second position represented by solid lines, where the elongate flexible medical member is ready for translational movement in the direction of branch 23*b*.

The elongate flexible medical member may be driven by the drive members in the movement or movements described above. The drive members may be arranged in pairs.

Now the third mode of operation will be presented, in relation to FIGS. 2*d* to 2*f*.

The catheter guide 15' and its bent end 15"*a* advance in translation T along the guide 15", while simultaneously the catheter guide 15" and its bent end 15"*a* are alternately rotated R about the axis of the catheter guide 15".

The three FIGS. 2*d*, 2*e* and 2*f* represent the curved end 15"*a* in different positions of angular orientation during the alternating rotation R.

The speed of the translation T is relatively slow, while the frequency of the alternating rotation R is relatively high. This third mode of operation, slow translation with simultaneous rapid alternating rotation, allows the catheter guide 15"*a* to easily pass sensitive or difficult areas in the circulatory system of the human body. It is the rapid rotation over a small translational distance that allows passing through the delicate area without jamming or catching on the wall of a patient's blood vessel.

Figure 3:
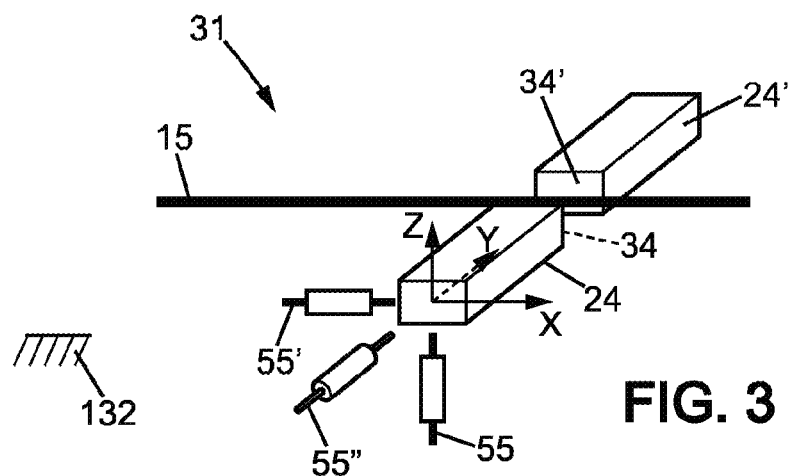
FIG. 3 is a schematic perspective view of a portion of a drive module in a free configuration.

In FIG. 3, a drive module 131 according to a first embodiment is represented. This drive module 131 is adapted to drive an elongate flexible medical member 15 extending in a longitudinal direction X. Note that the longitudinal direction X at the drive module 131 is not necessarily the same as that of the elongate flexible medical member 15 at its end but a translation and/or rotation of the elongate flexible medical member 15 along/about the longitudinal direction X at the drive module 131 will cause a respective translation and/or rotation of the elongate flexible medical member 15, along/about its longitudinal direction at its end.

The drive module 131 comprises a base 132 and at least one drive member 24 movably mounted relative to the base 132. Drive member 24 is for example movably mounted relative to the base 132.

In the example shown, the drive module 131 further comprises a second drive member 24'. Drive member 24, also referred to hereinafter as the first drive member, and second drive member 24', together form a pair of drive members 33. A pair of drive members 33 comprises two drive members which cooperate to generate a movement of the elongate flexible medical member relative to the base 132. In the example shown, the second drive member 24' is movably mounted relative to the base 132. The second drive member 24' is for example movably mounted relative to the base 132.

The first drive member 24 and the second drive member 24' are paired for simultaneous movements. For example, the first and second drive members 24, 24' can be individually controlled independently of one another, but according to respective synchronized commands. Alternatively, it is possible to provide a common command which will be distributed to each of the first and second drive members 24, 24' via a mechanical or electronic connection between their control systems.

Each drive member 24, 24' has a respective driving surface 34, 34'. The elongate flexible medical member 15 is placed between the driving surfaces 34, 34' of the drive members 24, 24' of the same pair. For clarity, the driving surfaces 34, 34' are shown apart from each other along direction Y.

The pair of drive members 24, 24' can be placed in a free configuration, shown in FIG. 5, in which the driving surface 34, 34' of the drive members 24, 24' of the pair of drive members 33 is not engaged with the elongate flexible medical member 15.

The pair of drive members 33 can be placed in a drive configuration, in which the driving surfaces 34, 34' of the drive members of the pair of drive members are engaged with the elongate flexible medical member 15 to be driven. The force applied by a drive member on the elongate flexible medical member in this configuration is for example a few Newtons (5-30 N for example). The return means, described above, are for example arranged to return the pair of drive members to the free configuration, which provides a safety function, for example in case of power failure.

To alternately place the pair of drive members 33 in the free and drive configurations, one can command a relative movement of the two drive members 24, 24' towards each other. This movement may for example be the movement of a drive member 24 relative to the base, the other remaining fixed. Alternatively, the two drive members 24, 24' may both move towards each other with respect to the base.

In the example, a movement in direction Y is provided.

In the embodiment shown, the two drive members 24, 24' are movable relative to the base with one degree of freedom. This degree of freedom differs from the one which allows alternately placing the drive members between the free and drive positions. In particular, it is provided that the drive members 24, 24' are movable relative to the base with one degree of freedom in their drive configuration. Thus, the movement of the drive members with one degree of freedom in their drive configuration generates a movement of the elongate flexible medical member with respect to the base 132.

An example will be described in more detail below in connection with FIGS. 4a to 4e. This example describes the generation of translational movement of the elongate flexible medical member along its longitudinal direction X.

Figure 4A:
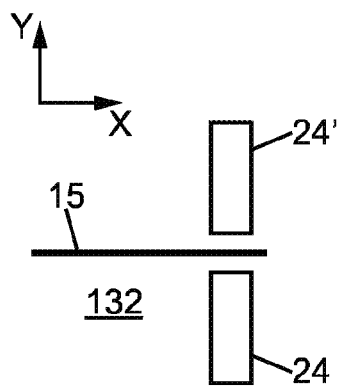
FIGS. 4a to 4e are simplified diagrams illustrating a catheter translation cycle according to one embodiment.
Figure 4B:
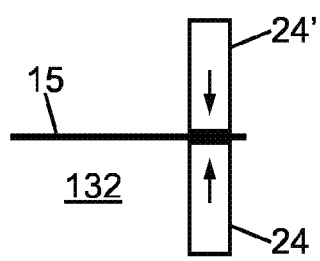

The starting position, shown in FIG. 4a, corresponds to that of FIG. 3 described above. The first transition is from the free configuration shown in FIG. 4a to the drive configuration (FIG. 4b). In the example, this transition is achieved by moving the two drive members in opposite directions along direction Y. The amplitude of this movement may depend on the elongate flexible medical member 15 to be driven. A guide, of smaller diameter than the catheter, may require a movement of greater amplitude than the catheter, from the same starting position.

Figure 4C:
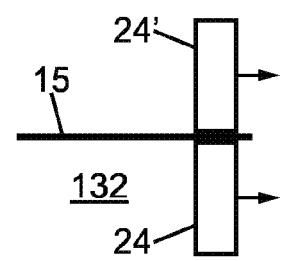

In the drive configuration, a simultaneous movement of the drive members is generated in the same direction along the longitudinal direction X, in a first direction of movement, which generates an identical movement of the elongate flexible medical member 15 (FIG. 4c).

Figure 4D:
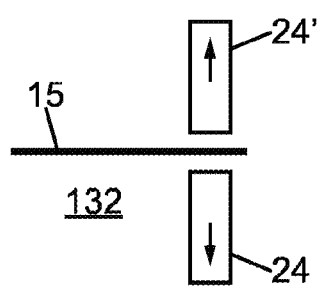

There is now a transition from the drive configuration shown in FIG. 4c to the free configuration (FIG. 4d). In the example, this transition occurs by moving the two drive members along direction Y in the opposite direction in order to transition the drive members from the drive configuration to the free configuration.

Figure 4E:
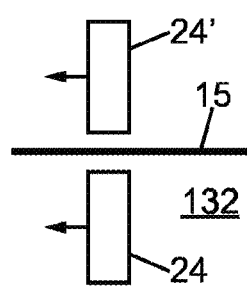

In the free configuration, a possibly simultaneous movement of the drive members is generated in a same direction along the longitudinal direction X, being a second direction of movement opposite to the first direction, which does not generate movement of the elongate flexible medical member 15 (FIG. 4e). This is a return to the initial configuration.

The above steps can be repeated in a cyclically controlled manner to generate translation of the elongate flexible medical member in a long path (for example several meters) along the longitudinal direction X, in the first direction of movement.

Movement of the elongate flexible medical member in a long path along the longitudinal direction X, in the second direction of movement, can be done by a series of operations which are the opposite of those just described.

The frequency of the cycle may be adjustable and controllable. In particular, it is possible to provide a low frequency for insertion of the elongate flexible medical member into the patient, or even several low frequency levels, in particular to enable slow navigation in difficult environments. A fast frequency can be provided, for example for withdrawal or even for emergency withdrawal. The amplitudes of movement for each cycle may also be adjustable.

For translational movements, speeds of between 0.1 and 200 millimeters per second are possible.

An example will be described in more detail below in relation to FIGS. 5a to 5e. This example describes the generation of a rotational movement of the elongate flexible medical member about its longitudinal direction X.

Figure 5A:
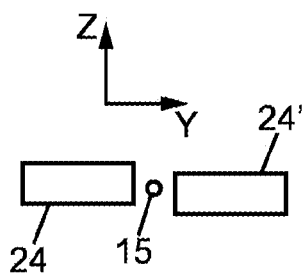
FIGS. 5a to 5e are simplified diagrams illustrating a catheter rotation cycle according to one embodiment.
Figure 5B:
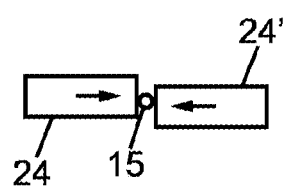

The starting position, shown in FIG. 5a, corresponds to that of FIG. 3 described above. In a first step, it transitions from the free configuration shown in FIG. 5a to the drive configuration (FIG. 5b). In the example, this transition occurs by moving the two drive members in opposite directions along direction Y. This transition is the same as was already described in relation to FIGS. 4a, 4b above.

In the drive configuration, a simultaneous movement of the drive members is generated in opposite directions along a direction Z transverse to the longitudinal direction X, different from direction Y, which generates a rotational movement of the elongate flexible medical member 15 (FIG. 5c) about the longitudinal direction X. In particular, the elongate flexible medical member rolls, preferably without sliding, on the driving surfaces 34, 34' of the drive members 24, 24'. Alternatively, one could move only one of the two drive members, the other remaining fixed.

Figure 5C:
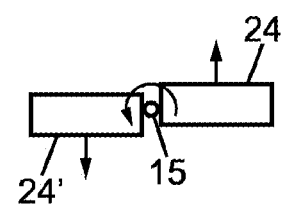
Figure 5D:
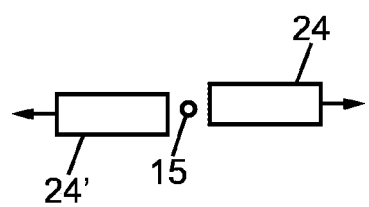

There is now a transition from the drive configuration shown in FIG. 5c to the free configuration (FIG. 5d). In the example, this transition occurs by moving the two drive members in opposite directions along direction Y, in the direction of movement opposite to the direction the drive members move from the drive configuration to the free configuration.

Figure 5E:
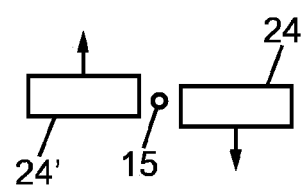

In the free configuration, a possibly simultaneous movement of the drive members is generated along direction Z, opposite to the movement described above in relation to FIG. 5c, which does not generate movement of the elongate flexible medical member 15 (FIG. 5e). This is a return to the initial configuration.

The above steps can be repeated in a cyclically controlled manner to generate rotation of the elongate flexible medical member in a long path (for example 360° multiple times) about the longitudinal direction X, in a first direction of rotation.

Movement of the elongate flexible medical member in a long path about the longitudinal direction X, in the second direction of rotation which is opposite to the first, can be done by a series of operations which are the opposite of those just described.

In the above description, the degree of rotation of the free end of the flexible medical member within the patient's body can be monitored by imaging. However, alternatively or additionally one can have upstream control of the amplitude of the rotation applied to the flexible medical member at the drive module. This requires knowledge of the diameter of the elongate flexible medical member at the drive members 24, 24'. Indeed, the angle of rotation of the elongate flexible medical member for a given movement of the actuating members depends on the ratio between the diameter of the elongate flexible medical member and the stroke of the drive members. This diameter can be predefined and stored in the control station 11. It is sufficient to inform the control station 11 beforehand of the type of catheter used, with the type including the diameter. Alternatively, the diameter of the elongate flexible medical member can be detected in situ. If the free configuration of each drive member constitutes a reference position, it is possible to know the position of the drive member in the drive configuration, for example by using a coding system on the actuator associated with each drive member and enabling movement of the drive member from its free configuration to its drive configuration.

By knowing the position of the two drive members in the drive configuration, and knowing the gap between the driving surfaces 34, 34' of the two drive members in their free configuration, it is possible to determine the gap between the two driving surfaces in the drive configuration and hence the diameter of the elongate flexible medical member.

This knowledge can also be used to detect the end of a withdrawal movement of the elongate flexible medical member. Indeed, if the control station 11 detects a sudden change in the diameter detected over time when controlling the withdrawal of the elongate flexible medical member, it presumably means that the elongate flexible medical member has been completely removed from the patient, and even from the module. The detected diameter then can either be zero or for example the diameter of the guide if the latter extends between the two drive members.

It is also possible to control the clamping force on the elongate flexible medical member in the drive configuration.

Indeed, in drive configuration, the current applied to the actuators is proportional to the clamping force applied to the elongate flexible medical member. Knowledge of this current therefore makes it possible to determine the clamping force applied to the catheter. In practice, it will be possible to provide at the control station 11 different current settings for the actuators, within an acceptable clamping range outside of which there is a risk of either the elongate flexible medical member sliding out of the grip, or of damaging the elongate flexible medical member by excessive mechanical stress exerted by the drive members.

The clamping of the elongate flexible medical member can be controlled for any movement applied to the catheter, not only for the rotational movement described above.

Determination of the diameter of the elongate flexible medical member could be done for catheter movement implementations other than the cyclic repeated commands described herein.

Thus, independently of the cyclic repeated commands described herein, it seems that another invention relates to a robotic module for driving an elongate flexible medical member, comprising:
- a base 132,
- a pair 33 of drive members 24, 24' each having a driving surface 34, 34', the pair 33 of drive members 24, 24' able to be positioned by at least one actuator 26 in a configuration in which the driving surfaces 34, 34' of the drive members 24, 24' of the pair 33 of drive members 24, 24' are engaged with the elongate flexible medical member to be driven and are arranged one on either side of it,
- the pair 33 of drive members 24, 24' being movably mounted relative to the base 132 with a degree of freedom between a first and a second position,
- a control member 18, 11 adapted to control, based on a representative signal relating to the actuator 26 (for example repeatedly cyclic), a movement relative to the base 132 of the drive members 24, 24' of the pair 33 of drive members 24, 24', from the first position to the second position into a drive configuration, thereby driving the elongate flexible medical member relative to the base 132.

In particular, the representative signal relating to the actuator makes it possible to determine a gap between the driving surfaces 34, 34', the control member 18, 11 controlling a movement determined from the gap relative to the base 132 of the drive members 24, 24' of the pair 33 of drive members 24, 24' thus causing a rotation of controlled amplitude of the elongate flexible medical member relative to the base 132.

In particular, the representative signal relating to the actuator makes it possible to control a clamping force applied to the elongate flexible medical member within a permissible range of clamping forces.

In the two embodiments above, a sequential movement is described during which the movement of a drive member in one direction is expected to be completed in order to begin another movement.

However, since the actuations of the drive members with various degrees of freedom can be independent by using the three actuating systems 55, 55', 55" described above independently, it would be possible to implement the movement of a drive member with two degrees of freedom simultaneously. For example, the movement of the drive members from the position of FIG. 5c to that of FIG. 5e could include an intermediate phase between a first phase of simple movement apart and a second phase of simple return to the initial position, where these two movements are combined. A similar intermediate phase can also be envisaged between the position of FIG. 5d and the position of FIG. 5b, between the phase of simple return to the initial position and a phase of simple movement closer together. Drawing the line, one could have no more phases of simple return to the initial position, simple movement apart, and simple movement closer together, as long as there is no risk of generating undesired movements in the elongate flexible medical member.

On the other hand, while a purely translational movement of the elongate flexible medical member has been presented independently in FIGS. 4a-4e, and a purely rotational movement in FIGS. 5a-5e, alternatively these two movements could be combined. With this current configuration, it would be sufficient to combine suitable movements of the drive members in order to generate simultaneous translation and rotation.

The previous example comprises a single pair of drive members.

Alternatively, one could provide multiple pairs of drive members. For example for descriptive purposes, two pairs of drive members could be provided. The drive members 24", 24''' of the second pair 33' may be similar to those of the first pair, and in particular have driving surfaces 34", 34''', and be actuated from the remote control station 11, or even the local control unit 18 using implementations similar to those for the first pair. The first pair 33 and the second pair 33' of drive members may be offset relative to each other along the longitudinal axis X of the elongate flexible medial member. According to a first example, the two pairs 33, 33' may be coplanar in their free configuration. In other words, they may be facing a base 132 common to both pairs. Alternatively, the bases 132, 132' of each pair could be independent or even non-coplanar.

Actuations of the two pairs can be synchronized. For example, actuations of the two pairs can generate identical simultaneous movements of the two pairs.

Alternatively, the two pairs can be actuated synchronously to generate phase shifted movements. In other words, a first pair 33 may be in the drive configuration while another pair is in the free configuration, and vice versa. For example, there is always at least one pair in the drive configuration. At any given moment, this may be the first, the second, or even both at the same time. Such a configuration improves the grip on the elongate flexible medical member. Particularly when the elongate flexible medical member is being moved while rubbing against an anatomical area of the patient, it must be possible to ensure a grip sufficient to overcome local resistance to the movement.

This is all the more difficult when the elongate flexible medical member is slippery, for example because it is kept in a solution.

Figure 6A:
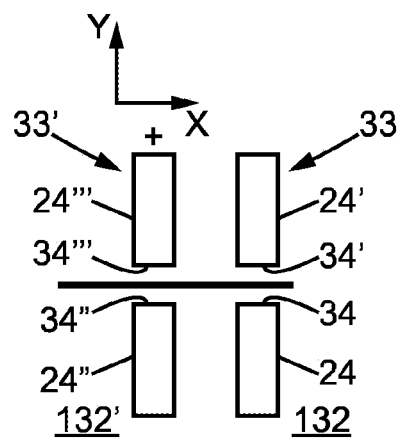
FIGS. 6a to 6f are simplified diagrams illustrating a catheter translation cycle according to one embodiment.
Figure 6B:
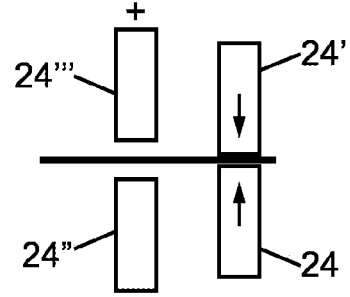
Figure 6C:
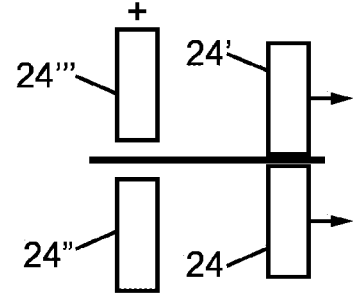
Figure 6D:
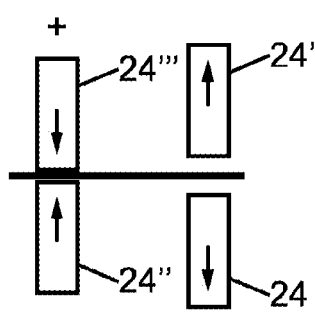
Figure 6E:
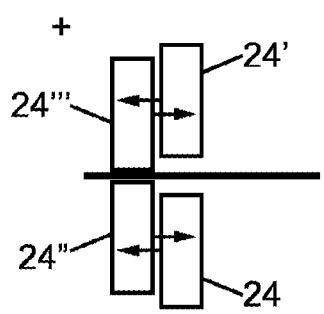
Figure 6F:
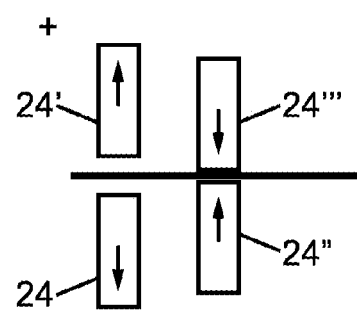

An illustrative example is given in FIGS. 6a to 6f for a translational driving mode. In these figures, a fixed reference over time is designated by the sign "+". The movement of the first pair, represented in FIGS. 6a to 6e, has already been described above in relation to FIGS. 4a to 4e. FIG. 6f shows the same position as FIG. 6b, the movement being cyclic.

FIGS. 6b to 6f show the movements of the second pair 33' during a cycle. These movements are phase-shifted relative to those of the first pair, the position illustrated in FIG. 6d for the second pair corresponding to that of FIG. 6b for the first pair, and so on.

The two pairs are spaced apart to avoid any collision, particularly as shown in FIG. 6e where the second pair is being moved in the direction which advances the elongate flexible medical member and where the first pair is being moved in the opposite direction.

By way of illustration, FIG. 6a can represent an initial state in which the two pairs are located at a distance from the elongate flexible medical member. When starting up the system the first pair will be controlled, and then the second pair in a phase-shifted manner.

This implementation applies for movements other than translation. This implementation applies for more than two pairs. In such case, where appropriate all pairs are phase-shifted relative to one another, or some pairs may be in phase with one another.

Figure 8:
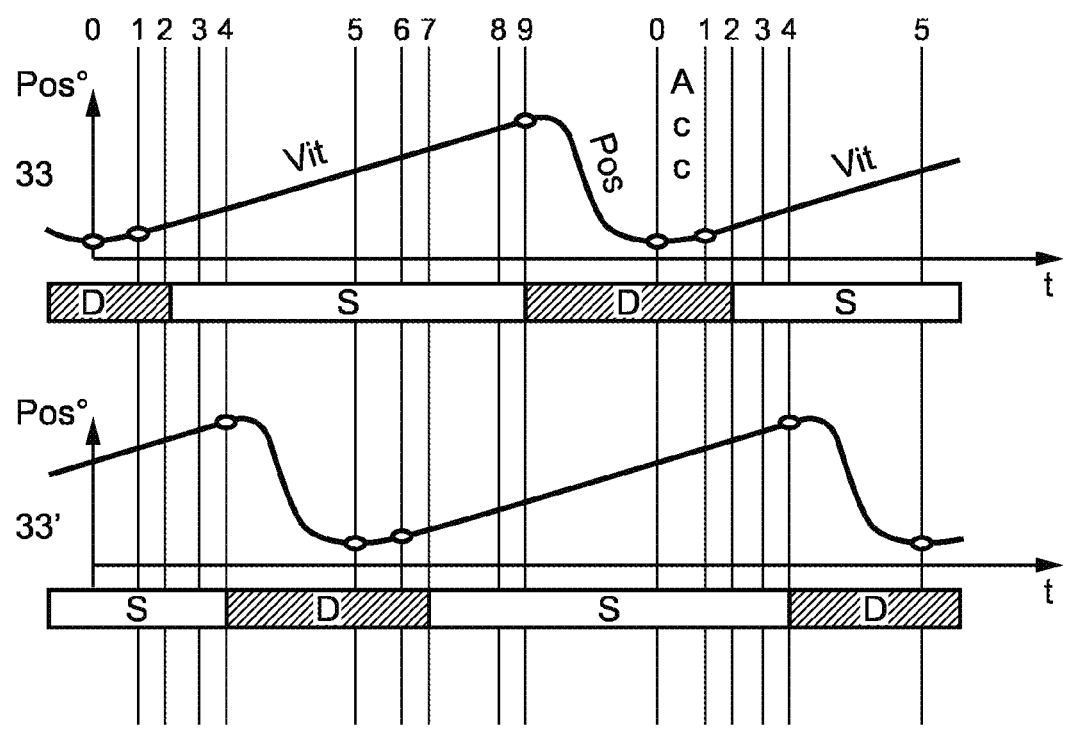

FIG. 8 describes a concrete example of synchronizing two pairs 33, 33'. The cycle below is described with reference to the first pair 33, keeping in mind that pair 33' is in phase opposition to said first pair.

Step 0: accelerate to reach target speed

Step 1: that speed being reached, maintain it at a constant level and send the clamping command, the goal being to reach effective clamping at the beginning of step 2; meanwhile, the second pair 33' is still at full speed with clamping enabled Step 2: enter clamping mode and remain at constant speed Step 3: remain in clamping mode and remain at constant speed; at this time, the second pair 33' receives the unclamping command, which will be effective at the beginning of step 4 after a certain delay (related to the mechanical and electronic response time of the system as a whole); in total, we can consider that we have had a period of simultaneous driving by the two pairs starting at the beginning of step 2 and ending at the beginning of step 4.

Step 3: remain in clamping mode and at constant speed;

Step 4: remain in clamping mode and at constant speed; during this time, the second pair 33' returns to its original position and waits, unmoving, at its original position; this wait time varies according to the selected speed of translation and rotation, and also the total cycle time.

Step 5: remain in clamping mode and at constant speed; the second pair 33' reaches the start of its cycle, which is the equivalent of step 0 for the first pair 33.

Step 6: remain in clamping mode and at constant speed; the second pair 33' ends its acceleration and reaches the beginning of the constant speed step (equivalent to step 1 for the first pair 33)

Step 7: remain in clamping mode and at constant speed; clamping takes effect for the second pair 33'

Step 8: send the unclamping command while keeping the speed constant; the unclamping command will necessarily require a certain period to take effect, and it is therefore necessary to continue at constant speed during this period;

Step 9: consider the unclamping to have taken effect, and send the command to return to the initial position in preparation for the next cycle, then once the return has occurred, wait at the initial position until the beginning of the next cycle.

In the case where the diameter of the elongate flexible medical member is detected with at least two pairs of drive members, it is possible to detect that the end of a step of withdrawing the elongate flexible medical member has been reached if two pairs of drive members allow determining different diameters. This will occur when an upstream pair still detects the presence of the elongate flexible medical member between its drive members while a downstream pair no longer detects it (no longer detects it whether a guide or nothing). Such detection makes it possible to stop controlling the downstream drive members if these are not driving the guide. Moreover, independently, such detection makes it possible to stop the complete withdrawal of the elongate flexible medical member when needed, which allows re-insertion of the elongate flexible medical member into the patient when appropriate, without manual intervention to reengage the elongate flexible medical member in the driving module.

In the embodiments described above, the drive members are arranged symmetrically with respect to a general center plane of the elongate flexible medical member.

The implementation just described schematically represents a non-limiting example of a combined implementation of movements of two drive members of the same pair in two degrees of freedom combined, a successive implementation of movements of two drive members of the same pair in two different degrees of freedom, and a combined implementation of two independent pairs of drive members.

A practical example of an implementation of such a system is presented below in relation to FIGS. 7a and 7b. This exemplary embodiment is provided solely to illustrate a concrete embodiment of an actuating system.

Figure 7A:
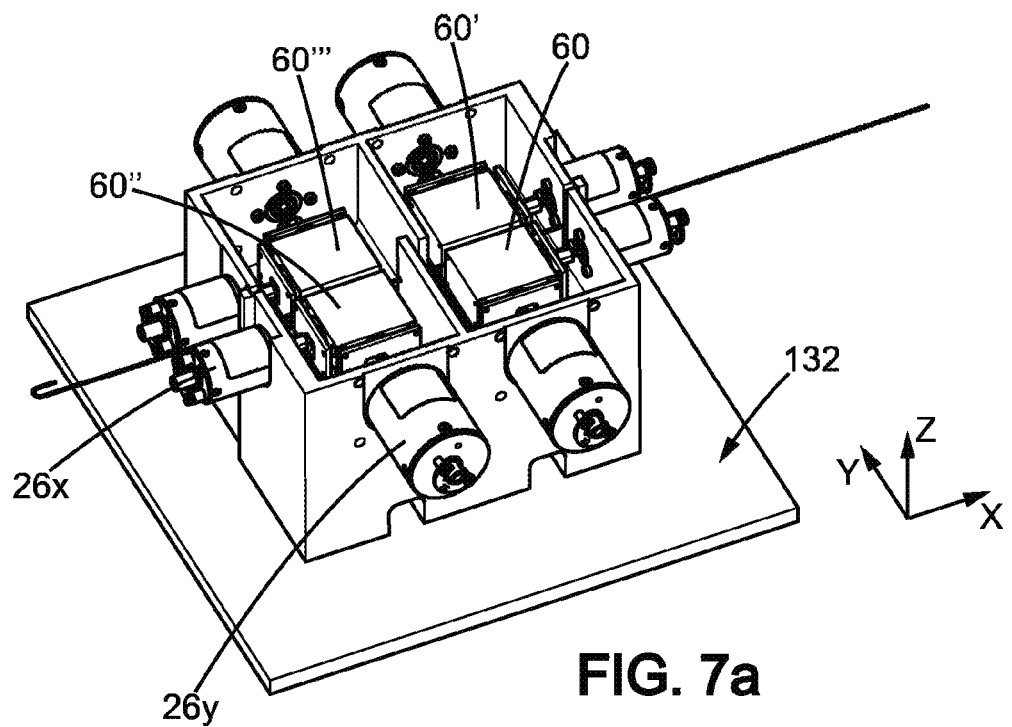
FIG. 7a is a perspective view of an exemplary embodiment of an actuating system.

FIG. 7a comprises a fixed base 132 common to four actuating systems. Each actuating system controls the movement of a respective drive member, not shown, but integral with a respective cube 60, 60', 60", 60'". The cubes 60, 60', 60", 60'" respectively correspond to the drive members 24, 24', 24", 24'" in FIG. 6a, substantially with the same orientation.

In the following, only the operation of one cube will be described. For example, we will refer to cube 60". Cube 60" is associated with three actuators 26x, 26y, 26z (the latter not visible, similar in all respects to actuators 26x and 26y, and located under the base 132. Actuator 26y is used to move cube 60" in direction Y while allowing movement of cube 60" simultaneously in directions X and Z relative to actuator 26y within a certain range of movement.

Figure 7B:
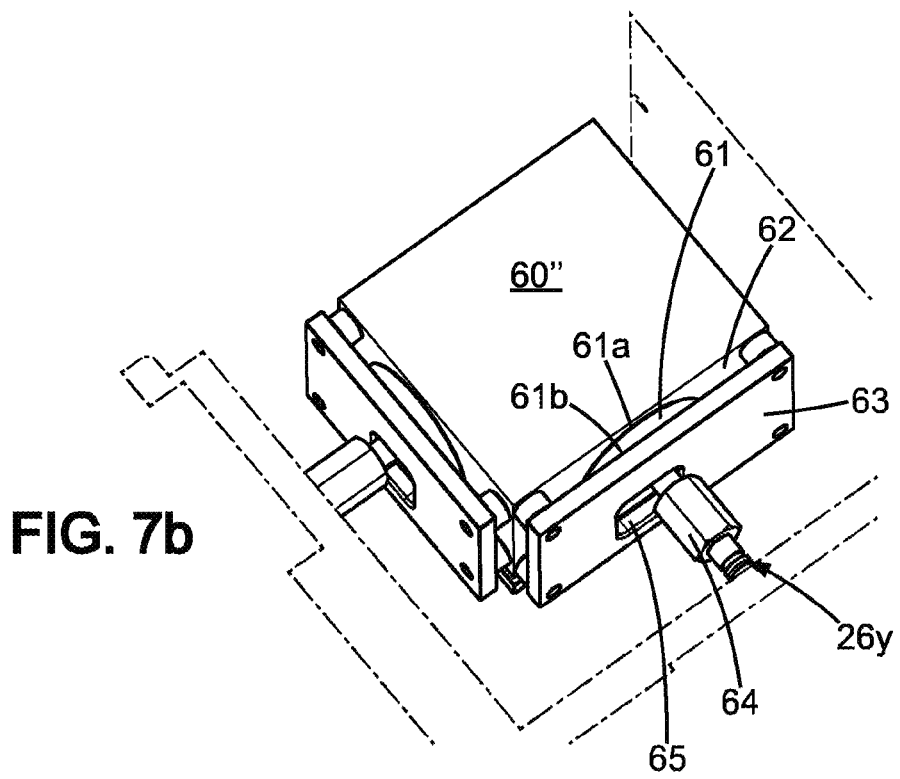
FIG. 7b is a detail view of FIG. 15a, FIG. 8 is a kinetic diagram of an example of driving in translation according to an exemplary embodiment, FIG. 9 schematically represents the evidence of stress exerted by the elongate flexible medical member on the drive members of the elongate flexible medical member, FIG. 10 schematically represents a first indirect method of stress detection by a robotic module for driving an elongate flexible member according to the invention, FIG. 11 schematically represents details of the implementation of the first indirect method of stress detection by a robotic module for driving an elongate flexible member according to the invention corresponding to FIG. 10, FIG. 12 schematically represents the first phase of a second direct method of stress detection by a robotic module for driving an elongate flexible member according to the invention, FIG. 13 schematically represents the second phase of a second direct method of stress detection by a robotic module for driving an elongate flexible member according to the invention, FIG. 14 schematically represents a third direct method of stress detection by a robotic module for driving an elongate flexible member according to the invention, FIG. 15 schematically represents a front view showing a fourth direct method of stress detection by a robotic module for driving an elongate flexible member according to the invention, FIG. 16 schematically represents a side view showing a fourth direct method of stress detection by a robotic module for driving an elongate flexible member according to the invention.

As can be seen in FIG. 7b, actuator 26y has an end integrally secured to a disk 61 of large diameter. This disc 61 is placed in a slot 62 formed between cube 60" and a plate 63 integrally secured thereto. In particular, the thickness of the slot 62 and disk 61 correspond, so that one surface 61a of the disk is in contact with cube 60" and the opposite surface 61b is in contact with the plate 63.

The arm 64 passes through a window 65 formed in the plate 63. The window 65 is shaped so that the disk 61 cannot exit the slot 62 through the window 65. The window 65 defines the authorized range of movement of the cube relative to actuator 26y in directions Y and Z.

The other actuators have a similar configuration for their respective orientations.

Therefore, for the extension of actuator 26y, the disk 61 pushes on cube 60" in direction Y and generates movement of the cube in that direction. When actuator 26y is retracted, the disc 61 pulls on the plate 63 in direction Y, and generates movement in that direction of cube 60" which is integral therewith. These movements are allowed within the range of movement allowed by the windows of the plates associated with actuators 26x and 26z.

When another actuator, for example actuator 26x, generates movement of cube 60" in direction X in the same manner, this movement is possible within the limits allowed by the dimension of the window 65 in direction X (and similarly for the plate associated with actuator 26z in this example).

Figure 9:
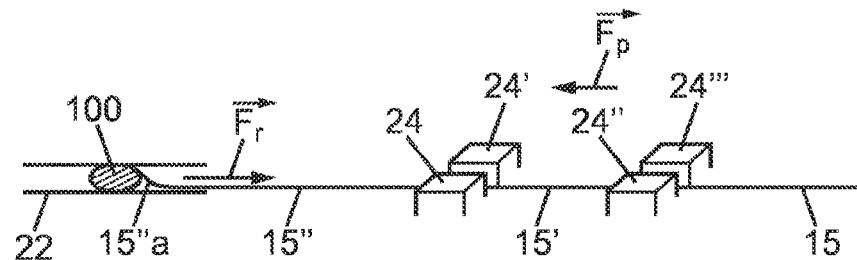

FIG. 9 schematically represents the manifestation of the stress exerted by the elongate flexible medical member on the drive members of said elongate flexible medical member.

An elongate flexible medical member, for example a catheter guide 15" terminated by a curved tip 15"', has advanced within a main artery 22 or within a branch of the artery, driven by drive members 24, 24', 24", 24"', as explained in more detail above in relation to the previous figures. As long as this elongate flexible medical member advances normally within the artery 22, it only exerts normal stress on the drive members 24, 24', 24", 24"'. Once this elongate flexible medical member 15 encounters an obstacle 100, such as a blood clot or stenosis for example, it no longer advances normally within the artery 22 and begins to exert abnormally high stress on the drive members 24, 24', 24", 24"' due to reaction force. This abnormally high stress exerted on the drive members 24, 24', 24", 24"' will be measurable. The measured stress can be transmitted in some manner to the user of the module for driving the elongate flexible medical member 15, in other words the catheter 15' and its guide 15". The user of the module for driving the elongate flexible medical member 15 will then, in response to this stress reported to the user, adapt his or her actions on the user interface of the module for driving the elongate flexible medical member 15, to modify the advancement of the elongate flexible medical member 15. Measurement of the reaction force on the elongate flexible medical member 15 displaced by the module for driving the elongate flexible medical member 15, which is in fact mainly the reaction force against the translational movement along the axis of the elongate flexible medical member 15, allows the user of the drive module to adjust his or her control of said drive module.

Figure 10:
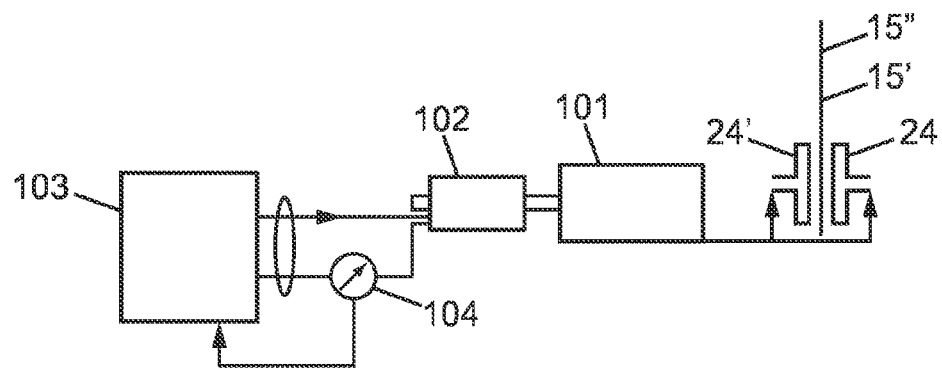

FIG. 10 schematically represents a first indirect method of stress detection by a robotic module for driving an elongate flexible member according to the invention.

Due to the obstacle encountered, a reaction force is applied to the elongate flexible medical member 15, this reaction force being converted into a stress exerted on the drive members 24 and 24'. This stress is passed on to the translational movement transmission mechanism 101 which drives the drive members 24 and 24'. This stress is then passed on to the actuator 102 which controls the translational movement mechanical transmission 101. An electronic source 103 supplies electric current to this actuator 102. An ammeter 104, placed on the electrical supply loop of this actuator 102, measures the electric current consumed by the actuator 102. This electric current consumed by the actuator 102 is representative of the stress exerted by the elongate flexible medical member 15 on the drive members 24 and 24'. The additional electric current consumed by the actuator 102 is representative of the excess stress exerted by the elongate flexible medical member 15 on the drive members 24 and 24' due to the obstacle encountered by the elongate flexible medical member 15. The user of the module for driving the elongate flexible medical member 15 will be informed, or even better will experience, this excess stress exerted by the elongate flexible medical member 15 on the drive members 24 and 24', and thus will be able to adapt his or her control of the module for driving the elongate flexible medical member 15.

Figure 11:
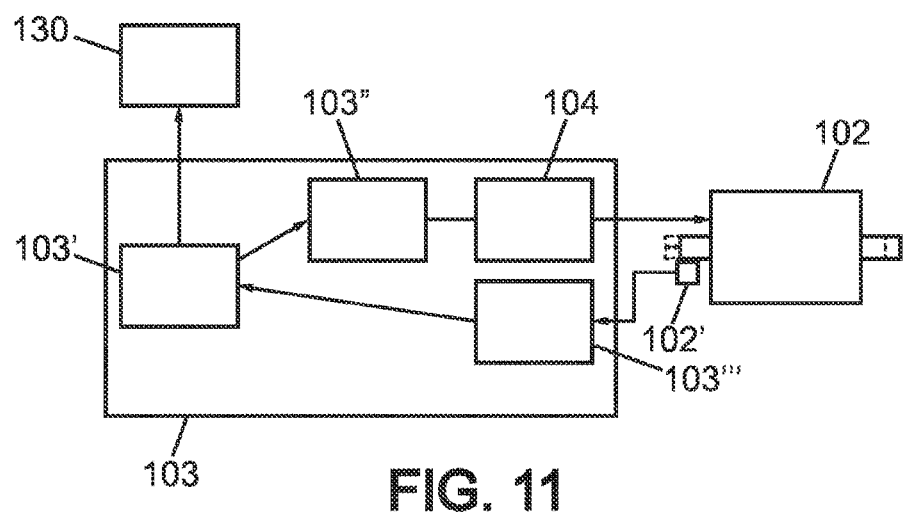

FIG. 11 schematically represents details of an implementation of the first indirect method of stress detection by a robotic module for driving an elongate flexible member according to the invention corresponding to FIG. 10.

An electronic system 103 drives an actuator 102. This circuit consists of a microcontroller 103', a variable voltage supply circuit 103", and a circuit 104 for measuring the current flowing in the voltage supply circuit 103". The actuator 102 is further provided with a position measuring sensor 102' connected to a reading circuit 103"' placed on the circuit board. The variable voltage supply circuit 103", the current measuring circuit 104, and the position sensor reading circuit 103"' are all connected to the microcontroller 103', which allows the microcontroller 103' to control the actuator 102. More specifically, the microcontroller 103' can control the position and speed of the actuator 102 at any moment, while measuring its power consumption in real time. However, the power consumption is an increasing function—possibly linear—of the thrust force of the actuator 102.

The thrust force $\vec{F_A}$ generated by the actuator 102 is transmitted to a transmission mechanism 101. By way of example, in the particular embodiment corresponding to FIG. 7b, this transmission mechanism 101 consists of the disc 61 and cube 60". The transmission mechanism 101 exerts a force $\vec{F_M}$ which opposes the thrust of the actuator 102 due to its inertia and internal friction. The transmission mechanism is connected to drive modules 24 and 24', more specifically to pads 107 and 108, which themselves drive the elongate flexible medical member 15 in the direction associated with the actuator 102. The elongate flexible medical member 15 itself exerts a resistance force $\vec{F_R}$ opposing the movement, which constitutes the reaction force to be measured.

As the forces involved are in equilibrium, this means that the thrust force of the actuator 102 is equal to the sum of the forces opposing it, namely:

$$\vec{F_A} = \vec{F_M} + \vec{F_R}$$

Thus:

$$\vec{F_R} = \vec{F_A} - \vec{F_M}$$

One therefore sees that the reaction force can be known from the measurement of the thrust force $F_A$ of the actuator 102 and the opposing force $F_M$ of the transmission mechanism 101.

Although the latter is not directly measurable, it can be modeled. Modeling the friction of a moving mechanical system is a problem known to those skilled in the art. One possible example of a model is to use the sum of a constant dry kinetic friction $F_C$ and a fluid friction $F_V$ proportional to the velocity:

$$\vec{F_M} = \vec{F_C} + \vec{F_V}$$

where $\vec{F_C} = \overrightarrow{\text{constant}}$ and: $\vec{F_V} = \mu.\vec{v}$, where $\vec{v}$ is the velocity and $\mu$ is the proportionality coefficient.

Other more elaborate models can be used. For example, we can distinguish between static dry friction (at zero velocity), whose value is greater than dynamic dry friction (at non-zero velocity), and whose value is proportional to the force of the thrust. It is also possible to take into account hysteresis phenomena generated by backlash. Models can also be used where the relationship between the fluid friction force and the velocity is non-linear. These examples are non-limiting, and another known modeling method can be used. In all cases, these models are based on the relationship between the force and the position of the actuator 102 measured by the sensor 102', on the one hand, and the velocity of the actuator 102 as deduced by deriving its position as a function of time, on the other hand. In all cases, the model will be based on the assumption that the friction forces $\vec{F_M}$ of a transmission mechanism, opposing the thrust of one or more actuators 102 with which it is interfaced, are a function of:

- the position of each actuator 102, measured by a sensor 102'
- the velocity of each actuator 102, deduced from the position by deriving the position as a function of time
- the thrust force $\vec{F_A}$ of each actuator on the drive mechanism.

One will further note that, when using multiple actuators, said friction force may be different for each actuator, which will then involve having one model per actuator or at least one set of particular parameters for each actuator, in order to be more precise.

Once the model is chosen, its parameters can be determined experimentally by measuring the force $F_M$ for different configurations and by identifying the parameters using a method known to those skilled in the art. An example of such a non-limiting method is the least squares method.

One will further note that if the position value used is that of the actuator 102, the modeled friction is that of the transmission mechanism 101 and not of the actuator 102. Indeed, the position of the internal elements of the transmission mechanism 101 is directly related to the position of the drive shaft of the actuator 102, as measured by the sensor 102', so that it is sufficient to use the position measurement of the sensor 102' for the model.

The microcontroller therefore has access to the following measurements:

1) The current $I_A$ consumed by the actuator 102
2) The position $x_A$ of the actuator 102

Then, calculating from these two measurements:

1) The thrust force $F_A$ exerted by the actuator 102, as a function of $I_A$
2) The velocity $V_A$ of the actuator 102 as a function of $x_A$
3) The opposing force of the drive mechanism $F_M$ as a function of $V_A$ and $x_A$;

this microcontroller is able to calculate the force $F_R$ of the reaction force, and to send this information to a user interface 130.

It should be noted that the formula $\vec{F_R} = \vec{F_A} - \vec{F_M}$ shows that the precise estimation of $\vec{F_R}$ assumes that the measurement and calculation errors involved in the estimation of $\vec{F_M}$ and $\vec{F_A}$ remain small compared to $\vec{F_R}$. In particular, if $\vec{F_A}$ and $\vec{F_M}$ are of the same order of magnitude in absolute value, their difference will be skewed by a potentially larger error. Note that this reasoning is strictly valid to the extent that the vectors $\vec{F_A}$ and $\vec{F_M}$ are collinear, the computations being reduced to the manipulation of algebraic values. On the other hand, if $\vec{F_M}$ is of low absolute value compared to $\vec{F_A}$, then the estimation error will have a smaller relative importance, and in the end the precision of the result will depend more on the precision of $\vec{F_A}$. Since the latter term is derived directly from the current measurement and not from modeling, it is easier to obtain a very precise value.

However, a low $\vec{F_M}$ value is the result of a transmission mechanism with little inertia and little friction.

Specifically, such a mechanism is obtained by the combined implementation of movements of two drive members of the same pair in two or three degrees of freedom combined, of which an exemplary practical implementation has been previously described and is illustrated by FIGS. 7a and 7b. Indeed, one of the particularly interesting effects is to enable transmission of a movement by multiple actuators, oriented in multiple spatial directions (for example three perpendicular axes X, Y and Z), to a single drive member with low friction and limited inertia.

However, this is not the case in conventional solutions, where it is usual to use a first actuator (for example X) connected to a drive member and mounted on a platform, said platform being driven by an actuator Y, the assembly being mounted on a second platform, said second platform being driven by an actuator Z. Thus, to drive the drive member along axis Z, actuator Z must drive a total of two platforms and two actuators: it must therefore drive significant weight, which generates significant inertia, and it must drive multiple interconnected mechanical elements, which generates a lot of friction. This configuration therefore does not allow obtaining a measurement of the reaction force with a precision comparable to the system described above.

Figure 12:
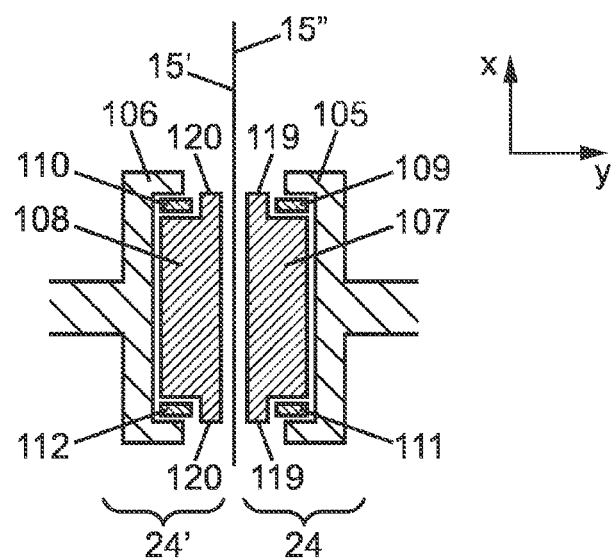

FIG. 12 schematically represents the first phase of a second direct method of stress detection by a robotic module for driving an elongate flexible member according to the invention. The X and Y axes are in the plane of FIG. 12, respectively parallel and perpendicular to the axis of the elongate flexible medical member 15.

The elongate flexible medical member 15 is driven along direction X, here by the drive members 24 and 24' which grip it by moving closer to one another along direction Y.

Drive member 24 comprises a receptacle-shaped pad holder 105 in which is fixed a pad 107 having flanges 119. In the empty spaces available between the periphery of the pad holder 105, the periphery of the pad 107, and the flanges 119 of the pad 107, are arranged elastic pieces 109 in the front part (in the upper part in FIG. 12) of drive member 24 and in the rear part 111 (in the lower part in FIG. 12) of drive member 24.

Drive member 24' comprises a receptacle-shaped pad holder 106 in which is fixed a pad 108 having flanges 120. In the empty spaces available between the periphery of the pad holder 106, the periphery of the pad 108, and the flanges 120 of the pad 108, are arranged elastic pieces 110 in the front part (in the upper part in FIG. 12) of drive member 24' and in the rear part 112 (in the lower part in FIG. 12) of drive member 24'.

When the pads 107 and 108 are brought closer together until they clasp the elongate flexible medical member 15, and the set of drive members 24 and 24' are moved forward parallel to direction X (upward in FIG. 12), the elongate flexible medical member 15 also advances (ascending upward in FIG. 12), and the elastic pieces 109, 110, 111 and 112 remain unexposed to stress or significant stress.

Figure 13:
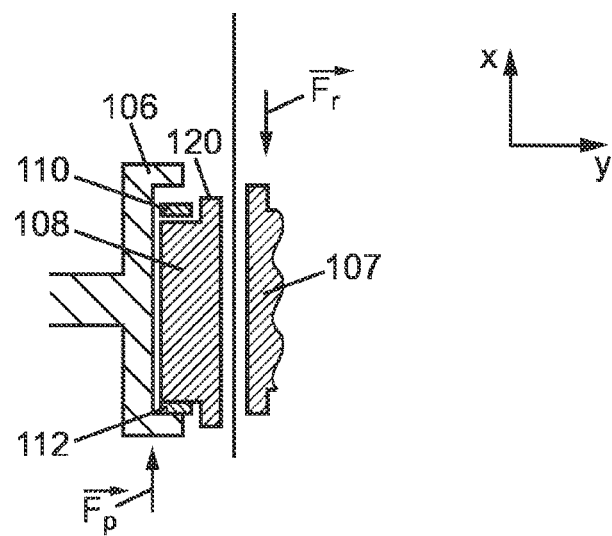

FIG. 13 schematically represents the second phase of a second direct method of stress detection by a robotic module for driving an elongate flexible member according to the invention.

When the pads 107 and 108 are brought closer together until they clasp the elongate flexible medical member 15, and the set of drive members 24 and 24' is moved forward parallel to direction X (upward in FIG. 12), the elongate flexible medical member 15 also advances (ascending upward in FIG. 12), unless it encounters an obstacle in which case the elongate flexible medical member 15 is slowed or blocked, tending to retain the pads 107 and 108, while their pad holders 105 and 106 continue to tend to advance, resulting in compression of the rear elastic pieces 111 and 112 although only the compression of piece 112 is shown, respectively between the periphery of pad 107 and the periphery of pad holder 105 on the one hand, and between the periphery of pad 108 and the periphery of pad holder 106 on the other hand.

This compression of the rear elastic pieces 111 and 112 is measurable and is measured, and is representative of the stress exerted by the elongate flexible medical member 15 on the drive members 24 and 24'. The elastic pieces, in particular 111 and 112 but also possibly 109 and 110, may for example be strain gauges or piezoelectric sensors.

FIG. 14 schematically represents a third direct method of stress detection by a robotic module for driving an elongate flexible member according to the invention.

This stress detection by a robotic module for driving an elongate flexible member functions similarly to that described for the second method in relation to FIGS. 11 and 12. The difference lies essentially in the structure of the sensor 110, which here is a pressure sensor. The elastic piece 110 is hollow and contains air or another gas. When the pad 108 presses against the pad holder 106 by a relative movement parallel to axis X, this hollow elastic piece 110 is compressed, and therefore the air contained in the compressed hollow elastic piece 110 is driven into the channel 113 which connects this elastic piece 110 to a pressure sensor 114. This air, initially contained in the compressed hollow elastic piece 110 and then driven into the channel 113, reaches the pressure sensor 114 at a positive pressure which is measured by the pressure sensor 114. This positive pressure measured by the pressure sensor 114 is representative of the stress exerted by the elongate flexible medical member 15 on the drive members 24 and 24', and it will therefore be used to construct the signal supplied to the user to assist the user in controlling the module for driving the elongate flexible medical member 15. In comparison to the strain gauges and piezoelectric sensors of FIGS. 11 and 12, this pressure sensor 114 offers the advantage of not requiring electrical connections near the elongate flexible medical member 15, but has the disadvantage of a somewhat more complicated structure due to the need to provide an air channel 113 within the structure of the pad holder 106.

FIG. 15 schematically represents a front view showing a fourth direct method of stress detection by a robotic module for driving an elongate flexible member according to the invention.

A pad 107 is carried by a pad holder 105. The pad holder 105 comprises a rigid frame 117 and a flexible piece 115, for example made of elastomer, the flexible piece 115 being centered in the rigid frame 117 by support bars 116 arranged along axis Y.

When the elongate flexible medical member 15 produces a reaction force on the pads, including pad 107, this pad 107 passes the received stress on to the flexible piece 115 which then tends to undergo a relative movement along axis X relative to the rigid frame 117.

FIG. 16 schematically represents a side view showing a fourth direct method of stress detection by a robotic module for driving an elongate flexible member according to the invention.

A strain gauge 118 is arranged between the rigid frame 117 and the flexible piece 115. This strain gauge 118 is attached to both the rigid frame 117 and the flexible piece 115. When the flexible piece 115 tends towards a relative movement along axis X relative to the rigid frame 117, after the pad 107 passes on the reaction force exerted on the elongate flexible medical member 15, the strain gauge 118 undergoes deformation caused by the relative movement of the flexible piece 115 with respect to the rigid frame 117. As a result, the strain gauge 118, which is fixed between the rigid frame 117 and the flexible piece 115, can therefore measure a stress representative of the reaction force and also representative of the stress exerted by the elongate flexible medical member 15 on the pads 107 and 108 in particular and on the drive members 24 and 24' in general.

The flexible piece 115 has been described as being part of the pad holder 105, as is the rigid frame 117. However, while the pad holder 105 is a permanent item, the pad 107 is a consumable item, usually changed with each manipulation. An alternative solution could be to integrate the flexible piece and/or the support bars 116 into the pad 107, making them consumable, and retaining only the rigid frame 117 and/or the support bars 116 as permanent elements because they are integrated into the pad holder 105.

The invention claimed is:

1. A robotic module for driving an elongate flexible medical member, comprising:
a pair of movable drive members alternately positionable in i) a drive configuration in which the drive members are sufficiently close together to drive the elongate flexible medical member and ii) a free configuration in which the drive members are sufficiently far apart so as not to drive the elongate flexible medical member;
a control member that controls, in a repeated cyclic manner, a forward movement of the drive members into the drive configuration in which the elongate flexible medical member is driven, and a reverse movement of the drive members into the free configuration in which the elongate flexible medical member is not driven;
a stress sensor structured and arranged to measure stress exerted by the elongate flexible medical member on at least one of the drive members;
a user interface linked to the stress sensor so as to receive the measured stress from the stress sensor, and configured to provide a signal representative of the measured stress to a user of the robotic module; and
actuators arranged to transmit movements in respective spatial directions toward each drive member by way of reversible transmission mechanisms, each one of said reversible transmission mechanisms configured such that:
if an actuator of said actuators makes a first movement to transmit a force to a drive member of said drive members which then performs a second movement, and if the drive member performs the second movement due to momentum from other than the actuator, the actuator is caused to perform the first movement.

2. The robotic module according to claim 1, wherein said signal comprises an indication that a threshold is exceeded by the measured stress.

3. The robotic module according to claim 2, wherein said signal comprises an indication of a value proportional to a value of the measured stress.

4. The robotic module according to claim 1, wherein said signal is implemented as at least one of a visual alarm and an audible alarm.

5. The robotic module according to claim 1, wherein said signal is implemented as at least one haptic feedback to the user of the robotic module, representative of the measured stress.

6. The robotic module according to claim 5, wherein said at least one haptic feedback is proportional to the measured stress.

7. The robotic module according to claim 5, wherein the at least one haptic feedback is adapted to reproduce a variation in the measured stress as low as 0.1 Newton.

8. The robotic module according to claim 1, further comprising:
an abnormal stress level estimator adapted to calculate a difference between said measured stress and a nominal stress corresponding to normal driving of the elongate flexible medical member by the drive members, whereby an exceeding of a threshold by said difference corresponding to an abnormal level of stress; and
a warning device that emits at least one of a visual alert and an audible alert upon exceeding said threshold.

9. The robotic module according to claim 1, wherein said stress sensor indirectly measures the stress exerted by the elongate flexible medical member on at least one of the drive members.

10. The robotic module according to claim 9, wherein said stress sensor measures current consumed by the drive members.

11. The robotic module according to claim 1, wherein said stress sensor directly measures the stress exerted by the elongate flexible medical member on at least one of the drive members.

12. The robotic module according to claim 11, wherein said stress sensor is a Hall effect sensor arranged to measure movement of a magnet arranged on one of the drive members.

13. The robotic module according to claim 1, wherein said stress sensor is a strain gauge arranged to directly measure the stress exerted by the elongate flexible medical member on the drive members.

14. The robotic module according to claim 13, wherein said strain gauge is arranged between a drive member and a frame of the robotic module, and is in contact with both said drive member and said frame of the robotic module.

15. The robotic module according to claim 13, wherein said strain gauge is arranged between two parts of said at least one of the drive members and is in simultaneous contact with the two parts of the drive member.

16. The robotic module according to claim 15, wherein:
the drive member comprises a pad configured to come into contact with the elongate flexible medical member, and a pad holder that transmits the movement to the pad,
said strain gauge arranged between said pad and said pad holder or between two portions of the pad holder.

17. The robotic module according to claim 16, wherein said strain gauge is arranged between a periphery of said pad and a periphery of said pad holder.

18. The robotic module according to claim 17, wherein said strain gauge is arranged between a bottom of said pad and a bottom of said pad holder.

19. The robotic module according to claim 1,
further comprising: a base,
wherein said drive members each have a driving surface,
wherein in said drive configuration the driving surfaces of the drive members are engaged with the elongate flexible medical member to be driven and are arranged one on either side thereof,
wherein in said free configuration the driving surfaces of the drive members are not engaged with the elongate flexible medical member, the drive members being movably mounted relative to the base with a degree of freedom between a first and a second position, and
wherein said control member controls, in a cyclic repeated manner, a forward movement relative to the base of the drive members from the first to the second position into the drive configuration thereby driving the elongate flexible medical member relative to the base, and a reverse movement relative to the base of the drive members from the second to the first position into the free configuration in which the elongate flexible medical member is not driven relative to the base.

20. The robotic module according to claim 19,
wherein the base is a first base, and said pair of drive members is a first pair of drive members,
and wherein the robotic module further comprises:
a second pair of drive members that each have a driving surface, the second pair of drive members being alternately positionable in a drive configuration in which the driving surfaces of the second pair of drive members engage with the elongate flexible medical member to be driven and are arranged one on either side thereof, and in a free configuration in which the driving surfaces of the second pair of drive members does not engage with the elongate flexible medical member, the second pair of drive members being movably mounted relative to the second base with a degree of freedom between a first and a second position,
the control member being further configured to control, in a cyclic repeated manner, a forward movement relative to the second base of the second pair of drive members from the first to the second position into the drive configuration thereby driving the elongate flexible medical member relative to the base, and a reverse movement relative to the base of the second pair of drive members from the second to the first position into the free configuration in which the flexible medical member is not driven relative to the base, said control member being configured to control the movements of the first and second pairs of the drive members in a synchronized manner.

21. The robotic module according to claim 1, wherein a translation of the drive members in a direction (Z) transverse to a local longitudinal direction (X) of the elongate flexible medical member and in opposite directions of movement is adapted to allow the elongate flexible medical member to roll on driving surfaces about the local longitudinal direction (X) of the elongate flexible medical member.

22. The robotic module according to claim 1, wherein the measured stress corresponds to the stress exerted by the elongate flexible medical member on at least one of the drive members only along the axis (X) of movement of the elongate flexible medical member.

23. A robotic module for driving an elongate flexible medical member, comprising:
- a pair of movable drive members alternately positionable in i) a drive configuration in which the drive members are sufficiently close together to drive the elongate flexible medical member and ii) a free configuration in which the drive members are sufficiently far apart so as not to drive the elongate flexible medical member;
- a control member that controls, in a repeated cyclic manner, a forward movement of the drive members into the drive configuration in which the elongate flexible medical member is driven, and a reverse movement of the drive members into the free configuration in which the elongate flexible medical member is not driven;
- a stress sensor structured and arranged to measure stress exerted by the elongate flexible medical member on at least one of the drive members;
  - a user interface linked to the stress sensor so as to receive the measured stress from the stress sensor, and configured to provide a signal representative of the measured stress to a user of the robotic module; and
- actuators arranged to transmit movements in respective spatial directions toward each drive member by way of reversible transmission mechanisms, each one of said reversible transmission mechanisms configured such that:
  - if an actuator of said actuators makes a first movement to transmit a force to a drive member of said drive members which then performs a second movement, and if the drive member performs the second movement due to momentum from other than the actuator, the actuator is caused to perform the first movement,
- wherein said stress sensor indirectly measures the stress exerted by the elongate flexible medical member on at least one of the drive members, and
- wherein said stress sensor measures the current consumed by said at least one of the drive members.

* * * * *